(12) United States Patent
Kellerman et al.

(10) Patent No.: US 7,892,251 B1
(45) Date of Patent: Feb. 22, 2011

(54) COMPONENT FOR DELIVERING AND LOCKING A MEDICAL DEVICE TO A GUIDE WIRE

(75) Inventors: Brad Kellerman, Escondido, CA (US); David H. Burkett, Temecula, CA (US); Robert Hayzelden, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2161 days.

(21) Appl. No.: 10/706,295

(22) Filed: Nov. 12, 2003

(51) Int. Cl.
*A61M 29/00* (2006.01)
(52) U.S. Cl. .................................... 606/200
(58) Field of Classification Search ............... 606/200; 279/2.17
See application file for complete search history.

(56) References Cited

U.S. PATENT DOCUMENTS

| | | | |
|---|---|---|---|
| 3,952,747 A | 4/1976 | Kimmell, Jr. | |
| 4,416,504 A * | 11/1983 | Sochor | 439/825 |
| 4,425,908 A | 1/1984 | Simon | |
| 4,494,531 A | 1/1985 | Gianturco | |
| 4,612,931 A | 9/1986 | Dormia | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,662,885 A | 5/1987 | DiPisa, Jr. | |
| 4,688,553 A | 8/1987 | Metals | |
| 4,706,671 A | 11/1987 | Weinrib | |
| 4,723,549 A | 2/1988 | Wholey et al. | |
| 4,727,873 A | 3/1988 | Mobin-Uddin | |
| 4,781,177 A | 11/1988 | Lebigot | |
| 4,790,812 A | 12/1988 | Hawkins, Jr. et al. | |
| 4,790,813 A | 12/1988 | Kensey | |
| 4,794,928 A | 1/1989 | Kletschka | |
| 4,832,055 A | 5/1989 | Palestrant | |
| 4,873,978 A | 10/1989 | Ginsburg | |
| 4,921,478 A | 5/1990 | Solano et al. | |
| 4,921,484 A | 5/1990 | Hillstead | |
| 4,969,891 A | 11/1990 | Gewertz | |

(Continued)

FOREIGN PATENT DOCUMENTS

EP 0427429 A3 9/1991

(Continued)

OTHER PUBLICATIONS

Dilitation of the Carotid Artery By A Temporary Carotid Filter By A. Beck, St. Milic, A.M. Spagnoli, November-December Issue of OPLITAI, An International Journal on Military Medicine and Health Emergencies, pp. 67-74.

*Primary Examiner*—Eduardo C Robert
*Assistant Examiner*—Michael G Mendoza
(74) *Attorney, Agent, or Firm*—Fulwider Patton LLP; Jonathan Feuchtwang

(57) ABSTRACT

A locking component delivers and locks an attached medical device along a pre-deployed guide wire. The locking component can lock onto a flexible body member disposed on the guide wire, such as the distal helical tip coil of a conventional guide or a specially-designed guide wire. The locking component includes a tapered opening which temporarily compresses a portion of the helical coil and a locking recess in communication with the tapered opening for receiving the compressed coil. Compressed coils which enter the locking recess will spring back to their original shape (diameter) within the locking recess, locking the component to the coil.

35 Claims, 5 Drawing Sheets

U.S. PATENT DOCUMENTS

| | | |
|---|---|---|
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maahs |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,562 A * | 8/1999 | Christensson ............... 439/729 |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |

| Patent | Type | Date | Inventor |
|---|---|---|---|
| 6,336,934 | B1 | 1/2002 | Gilson et al. |
| 6,340,364 | B2 | 1/2002 | Kanesaka |
| 6,340,465 | B1 | 1/2002 | Hsu et al. |
| 6,346,116 | B1 | 2/2002 | Brooks et al. |
| 6,348,056 | B1 | 2/2002 | Bates et al. |
| 6,355,051 | B1 | 3/2002 | Sisskind et al. |
| 6,361,545 | B1 | 3/2002 | Macoviak et al. |
| 6,361,546 | B1 | 3/2002 | Khosravi |
| 6,364,895 | B1 | 4/2002 | Greenhalgh |
| 6,364,896 | B1 | 4/2002 | Addis |
| 6,371,969 | B1 | 4/2002 | Tsugita et al. |
| 6,371,970 | B1 | 4/2002 | Khosravi et al. |
| 6,371,971 | B1 | 4/2002 | Tsugita et al. |
| 6,375,670 | B1 | 4/2002 | Greenhalgh |
| 6,383,206 | B1 | 5/2002 | Gillick et al. |
| 6,384,062 | B1 | 5/2002 | Ikeda et al. |
| 6,391,044 | B1 | 5/2002 | Yadav et al. |
| 6,394,978 | B1 | 5/2002 | Boyle et al. |
| 6,395,014 | B1 | 5/2002 | Macoviak et al. |
| 6,398,756 | B2 | 6/2002 | Peterson et al. |
| 6,402,771 | B1 | 6/2002 | Palmer et al. |
| 6,406,471 | B1 | 6/2002 | Jang et al. |
| 6,423,032 | B2 | 7/2002 | Parodi |
| 6,423,086 | B1 | 7/2002 | Barbut et al. |
| 6,425,909 | B1 | 7/2002 | Dieck et al. |
| 6,428,559 | B1 | 8/2002 | Johnson |
| 6,432,122 | B1 | 8/2002 | Gilson et al. |
| 6,436,121 | B1 | 8/2002 | Blom |
| 6,443,926 | B1 | 9/2002 | Kletschka |
| 6,443,971 | B1 | 9/2002 | Boylan et al. |
| 6,443,972 | B1 | 9/2002 | Bosma |
| 6,443,979 | B1 | 9/2002 | Stalker et al. |
| 6,447,530 | B1 | 9/2002 | Ostrovsky et al. |
| 6,447,531 | B1 | 9/2002 | Amplatz |
| 6,450,989 | B2 | 9/2002 | Dubrul et al. |
| 6,458,139 | B1 | 10/2002 | Palmer et al. |
| 6,461,370 | B1 | 10/2002 | Gray et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,497 | B2 | 11/2002 | Wensel et al. |
| 6,485,500 | B1 | 11/2002 | Kokish et al. |
| 6,485,501 | B1 | 11/2002 | Green |
| 6,485,502 | B2 | 11/2002 | Don Michael et al. |
| 6,485,507 | B1 | 11/2002 | Walak et al. |
| 6,494,895 | B2 | 12/2002 | Addis |
| 6,499,487 | B1 | 12/2002 | McKenzie et al. |
| 6,500,166 | B1 | 12/2002 | Zadno Azizi et al. |
| 6,506,203 | B1 | 1/2003 | Boyle et al. |
| 6,506,205 | B2 | 1/2003 | Goldberg et al. |
| 6,511,492 | B1 | 1/2003 | Rosenbluth |
| 6,511,496 | B1 | 1/2003 | Huter et al. |
| 6,511,497 | B1 | 1/2003 | Braun et al. |
| 6,511,503 | B1 | 1/2003 | Burkett et al. |
| 6,514,273 | B1 | 2/2003 | Voss et al. |
| 6,517,550 | B1 | 2/2003 | Konya et al. |
| 6,517,559 | B1 | 2/2003 | O'Connell |
| 6,520,978 | B1 | 2/2003 | Blackledge et al. |
| 6,527,746 | B1 | 3/2003 | Oslund et al. |
| 6,527,791 | B2 | 3/2003 | Fisher |
| 6,530,939 | B1 | 3/2003 | Hopkins et al. |
| 6,530,940 | B2 | 3/2003 | Fisher |
| 6,533,800 | B1 | 3/2003 | Barbut |
| 6,537,294 | B1 | 3/2003 | Boyle et al. |
| 6,537,295 | B2 | 3/2003 | Petersen |
| 6,537,296 | B2 | 3/2003 | Levinson et al. |
| 6,537,297 | B2 | 3/2003 | Tsugita et al. |
| 6,540,722 | B1 | 4/2003 | Boyle et al. |
| 6,540,767 | B1 | 4/2003 | Walak et al. |
| 6,540,786 | B2 | 4/2003 | Diaz et al. |
| 6,544,276 | B1 | 4/2003 | Azizi |
| 6,544,279 | B1 | 4/2003 | Hopkins et al. |
| 6,544,280 | B1 | 4/2003 | Daniel et al. |
| 6,547,759 | B1 | 4/2003 | Fisher |
| 6,551,268 | B1 | 4/2003 | Kaganov et al. |
| 6,551,341 | B2 | 4/2003 | Boylan et al. |
| 6,551,342 | B1 | 4/2003 | Shen et al. |
| 6,558,401 | B1 | 5/2003 | Azizi |
| 6,558,405 | B1 | 5/2003 | McInnes |
| 6,562,058 | B2 | 5/2003 | Seguin et al. |
| 6,565,591 | B2 | 5/2003 | Kelly et al. |
| 6,569,184 | B2 | 5/2003 | Huter |
| 6,575,995 | B1 | 6/2003 | Huter et al. |
| 6,575,996 | B1 | 6/2003 | Denison et al. |
| 6,575,997 | B1 | 6/2003 | Palmer et al. |
| 6,582,447 | B1 | 6/2003 | Patel et al. |
| 6,582,448 | B1 | 6/2003 | Boyle et al. |
| 6,585,756 | B1 | 7/2003 | Strecker |
| 6,589,263 | B1 | 7/2003 | Hopkins et al. |
| 6,589,265 | B1 | 7/2003 | Palmer et al. |
| 6,592,546 | B1 | 7/2003 | Barbut et al. |
| 6,592,606 | B2 | 7/2003 | Huter et al. |
| 6,592,607 | B1 | 7/2003 | Palmer et al. |
| 6,592,616 | B1 | 7/2003 | Stack et al. |
| 6,596,011 | B2 | 7/2003 | Johnson et al. |
| 6,599,307 | B1 | 7/2003 | Huter et al. |
| 6,599,308 | B2 | 7/2003 | Amplatz |
| 6,602,269 | B2 | 8/2003 | Wallace et al. |
| 6,602,271 | B2 | 8/2003 | Adams et al. |
| 6,602,272 | B2 | 8/2003 | Boylan et al. |
| 6,602,273 | B2 | 8/2003 | Marshall |
| 6,605,102 | B1 | 8/2003 | Mazzocchi et al. |
| 6,605,111 | B2 | 8/2003 | Bose et al. |
| 6,607,506 | B2 | 8/2003 | Kletschka |
| 6,610,077 | B1 | 8/2003 | Hancock et al. |
| 6,616,679 | B1 | 9/2003 | Khosravi et al. |
| 6,616,680 | B1 | 9/2003 | Thielen |
| 6,616,681 | B2 | 9/2003 | Hanson et al. |
| 6,616,682 | B2 | 9/2003 | Joergensen et al. |
| 6,620,148 | B1 | 9/2003 | Tsugita et al. |
| 6,620,182 | B1 | 9/2003 | Khosravi |
| 6,623,450 | B1 | 9/2003 | Dutta |
| 6,629,953 | B1 | 10/2003 | Boyd |
| 6,632,236 | B2 | 10/2003 | Hogendijk |
| 6,632,241 | B1 | 10/2003 | Hancock et al. |
| 6,635,068 | B1 | 10/2003 | Dubrul et al. |
| 6,635,070 | B2 | 10/2003 | Leeflang et al. |
| 6,638,293 | B1 | 10/2003 | Makower et al. |
| 6,638,294 | B1 | 10/2003 | Palmer |
| 6,645,220 | B1 | 11/2003 | Huter et al. |
| 6,645,221 | B1 | 11/2003 | Richter |
| 6,645,223 | B2 | 11/2003 | Boyle et al. |
| 6,645,224 | B2 | 11/2003 | Gilson et al. |
| 6,652,480 | B1 | 11/2003 | Imran et al. |
| 6,652,505 | B1 | 11/2003 | Tsugita et al. |
| 6,652,554 | B1 | 11/2003 | Wholey et al. |
| 6,652,557 | B1 | 11/2003 | MacDonald |
| 6,656,202 | B2 | 12/2003 | Papp et al. |
| 6,656,203 | B2 | 12/2003 | Roth et al. |
| 6,656,204 | B2 | 12/2003 | Ambrisco et al. |
| 6,656,351 | B2 | 12/2003 | Boyle |
| 6,660,021 | B1 | 12/2003 | Palmer et al. |
| 6,663,650 | B2 | 12/2003 | Sepetka et al. |
| 6,663,651 | B2 | 12/2003 | Krolik et al. |
| 6,663,652 | B2 | 12/2003 | Daniel et al. |
| 6,673,090 | B2 | 1/2004 | Root et al. |
| 6,676,666 | B2 | 1/2004 | Vrba et al. |
| 6,676,682 | B1 | 1/2004 | Tsugita et al. |
| 6,676,683 | B1 | 1/2004 | Addis |
| 6,679,902 | B1 | 1/2004 | Boyle et al. |
| 6,679,903 | B2 | 1/2004 | Kurz |
| 6,682,546 | B2 | 1/2004 | Amplatz |
| 6,685,722 | B1 | 2/2004 | Rosenbluth et al. |
| 6,689,151 | B2 | 2/2004 | Becker et al. |
| 6,692,513 | B2 | 2/2004 | Streeter et al. |
| 6,695,813 | B1 | 2/2004 | Boyle et al. |

| Patent No. | Date | Inventor(s) |
|---|---|---|
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boyle et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,019 B2 | 1/2006 | Mazzocchi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Peterson |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Boyle et al. |
| 7,097,651 B2 | 8/2006 | Harrison et al. |
| 7,101,379 B2 | 9/2006 | Gregory, Jr et al. |
| 7,101,380 B2 | 9/2006 | Khachin et al. |
| 7,108,707 B2 | 9/2006 | Huter et al. |
| 7,331,973 B2 * | 2/2008 | Gesswein et al. ........... 606/200 |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111659 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |

| | | | | | | |
|---|---|---|---|---|---|---|
| 2002/0161392 A1 | 10/2002 | Dubrul | | 2003/0176886 A1 | 9/2003 | Wholey et al. |
| 2002/0161393 A1 | 10/2002 | Demond et al. | | 2003/0176889 A1 | 9/2003 | Boyle et al. |
| 2002/0161395 A1 | 10/2002 | Douk et al. | | 2003/0181942 A1 | 9/2003 | Daniel et al. |
| 2002/0165576 A1 | 11/2002 | Boyle et al. | | 2003/0181943 A1 | 9/2003 | Keegan et al. |
| 2002/0169414 A1 | 11/2002 | Kletschka | | 2003/0187474 A1 | 10/2003 | Keegan et al. |
| 2002/0169458 A1 | 11/2002 | Connors, III | | 2003/0187475 A1 | 10/2003 | Tsugita et al. |
| 2002/0169472 A1 | 11/2002 | Douk et al. | | 2003/0187495 A1 | 10/2003 | Cully et al. |
| 2002/0169474 A1 | 11/2002 | Kusleika et al. | | 2003/0191493 A1 | 10/2003 | Epstein et al. |
| 2002/0173815 A1 | 11/2002 | Hogendijk et al. | | 2003/0195554 A1 | 10/2003 | Shen et al. |
| 2002/0173817 A1 | 11/2002 | Kletschka et al. | | 2003/0195555 A1 | 10/2003 | Khairkhahan et al. |
| 2002/0188313 A1 | 12/2002 | Johnson et al. | | 2003/0195556 A1 | 10/2003 | Stack et al. |
| 2002/0188314 A1 | 12/2002 | Anderson et al. | | 2003/0199819 A1 | 10/2003 | Beck |
| 2002/0193825 A1 | 12/2002 | McGuckin et al. | | 2003/0199921 A1 | 10/2003 | Palmer et al. |
| 2002/0193826 A1 | 12/2002 | McGuckin et al. | | 2003/0204168 A1 | 10/2003 | Bosme et al. |
| 2002/0193827 A1 | 12/2002 | McGuckin et al. | | 2003/0204202 A1 | 10/2003 | Palmer et al. |
| 2002/0193828 A1 | 12/2002 | Griffin et al. | | 2003/0208222 A1 | 11/2003 | Zadno-Azizi |
| 2003/0004536 A1 | 1/2003 | Boylan et al. | | 2003/0208224 A1 | 11/2003 | Broome |
| 2003/0004537 A1 | 1/2003 | Boyle et al. | | 2003/0208225 A1 | 11/2003 | Goll et al. |
| 2003/0004539 A1 | 1/2003 | Linder et al. | | 2003/0208226 A1 | 11/2003 | Bruckheimer et al. |
| 2003/0004540 A1 | 1/2003 | Linder et al. | | 2003/0208227 A1 | 11/2003 | Thomas |
| 2003/0004541 A1 | 1/2003 | Linder et al. | | 2003/0208228 A1 | 11/2003 | Gilson et al. |
| 2003/0009188 A1 | 1/2003 | Linder et al. | | 2003/0208229 A1 | 11/2003 | Kletschka |
| 2003/0009189 A1 | 1/2003 | Gilson et al. | | 2003/0212361 A1 | 11/2003 | Boyle et al. |
| 2003/0015206 A1 | 1/2003 | Roth et al. | | 2003/0212429 A1 | 11/2003 | Keegan et al. |
| 2003/0018354 A1 | 1/2003 | Roth et al. | | 2003/0212431 A1 | 11/2003 | Brady et al. |
| 2003/0023265 A1 | 1/2003 | Forber | | 2003/0212434 A1 | 11/2003 | Thielen |
| 2003/0028238 A1 | 2/2003 | Burkett et al. | | 2003/0216774 A1 | 11/2003 | Larson |
| 2003/0032941 A1 | 2/2003 | Boyle et al. | | 2003/0220665 A1 | 11/2003 | Eskuri et al. |
| 2003/0032977 A1 | 2/2003 | Brady et al. | | 2003/0225418 A1 | 12/2003 | Eskuri et al. |
| 2003/0040772 A1 | 2/2003 | Hyodoh et al. | | 2003/0225435 A1 | 12/2003 | Huter et al. |
| 2003/0042186 A1 | 3/2003 | Boyle et al. | | 2003/0229295 A1 | 12/2003 | Houde et al. |
| 2003/0045898 A1 | 3/2003 | Harrison et al. | | 2003/0229374 A1 | 12/2003 | Brady et al. |
| 2003/0057156 A1 | 3/2003 | Peterson et al. | | 2003/0233117 A1 | 12/2003 | Adams et al. |
| 2003/0060782 A1 | 3/2003 | Bose et al. | | 2003/0236545 A1 | 12/2003 | Gilson |
| 2003/0060843 A1 | 3/2003 | Boucher | | 2004/0002730 A1 | 1/2004 | Denison et al. |
| 2003/0060844 A1 | 3/2003 | Borillo et al. | | 2004/0006361 A1 | 1/2004 | Boyle et al. |
| 2003/0065354 A1 | 4/2003 | Boyle et al. | | 2004/0006364 A1 | 1/2004 | Ladd |
| 2003/0069596 A1 | 4/2003 | Eskuri | | 2004/0006365 A1 | 1/2004 | Brady et al. |
| 2003/0069597 A1 | 4/2003 | Petersen | | 2004/0006366 A1 | 1/2004 | Huter et al. |
| 2003/0078519 A1 | 4/2003 | Salahieh et al. | | 2004/0006367 A1 | 1/2004 | Johnson et al. |
| 2003/0078614 A1 | 4/2003 | Salahieh et al. | | 2004/0006368 A1 | 1/2004 | Mazzocchi et al. |
| 2003/0083692 A1 | 5/2003 | Vrba et al. | | 2004/0015184 A1 | 1/2004 | Boyle et al. |
| 2003/0083693 A1 | 5/2003 | Daniel et al. | | 2004/0019363 A1 | 1/2004 | Hanson et al. |
| 2003/0100917 A1 | 5/2003 | Boyle et al. | | 2004/0034385 A1 | 2/2004 | Gilson et al. |
| 2003/0100918 A1 | 5/2003 | Duane | | 2004/0039411 A1 | 2/2004 | Gilson et al. |
| 2003/0105484 A1 | 6/2003 | Boyle et al. | | 2004/0044359 A1 | 3/2004 | Renati et al. |
| 2003/0109824 A1 | 6/2003 | Anderson et al. | | 2004/0044360 A1 | 3/2004 | Lowe |
| 2003/0114879 A1 | 6/2003 | Euteneuer et al. | | 2004/0049226 A1 | 3/2004 | Keegan et al. |
| 2003/0114880 A1 | 6/2003 | Hansen et al. | | 2004/0059372 A1 | 3/2004 | Tsugita |
| 2003/0120303 A1 | 6/2003 | Boyle et al. | | 2004/0059373 A1 | 3/2004 | Shapiro et al. |
| 2003/0130680 A1 | 7/2003 | Russell | | 2004/0082697 A1 | 4/2004 | Broome et al. |
| 2003/0130681 A1 | 7/2003 | Ungs | | 2004/0082968 A1 | 4/2004 | Krolik et al. |
| 2003/0130682 A1 | 7/2003 | Broome et al. | | 2004/0088000 A1 | 5/2004 | Muller |
| 2003/0130684 A1 | 7/2003 | Brady et al. | | 2004/0088002 A1 | 5/2004 | Boyle et al. |
| 2003/0130685 A1 | 7/2003 | Daniel et al. | | 2004/0093009 A1 | 5/2004 | Denison et al. |
| 2003/0130686 A1 | 7/2003 | Daniel et al. | | 2004/0093010 A1 | 5/2004 | Gesswein et al. |
| 2003/0130687 A1 | 7/2003 | Daniel et al. | | 2004/0093011 A1 | 5/2004 | Vrba |
| 2003/0130688 A1 | 7/2003 | Daniel et al. | | 2004/0093012 A1 | 5/2004 | Cully et al. |
| 2003/0135162 A1 | 7/2003 | Deyette, Jr. et al. | | 2004/0093013 A1 | 5/2004 | Brady et al. |
| 2003/0135232 A1 | 7/2003 | Douk et al. | | 2004/0098022 A1 | 5/2004 | Barone |
| 2003/0139764 A1 | 7/2003 | Levinson et al. | | 2004/0098026 A1 | 5/2004 | Joergensen et al. |
| 2003/0144685 A1 | 7/2003 | Boyle et al. | | 2004/0098032 A1 | 5/2004 | Papp et al. |
| 2003/0150821 A1 | 8/2003 | Bates et al. | | 2004/0098033 A1 | 5/2004 | Leeflang et al. |
| 2003/0153935 A1 | 8/2003 | Mialhe | | 2004/0102807 A1 | 5/2004 | Kusleika et al. |
| 2003/0153942 A1 | 8/2003 | Wang et al. | | 2004/0106944 A1 | 6/2004 | Daniel et al. |
| 2003/0153943 A1 | 8/2003 | Michael et al. | | 2004/0111111 A1 | 6/2004 | Lin |
| 2003/0158574 A1 | 8/2003 | Esch et al. | | 2004/0116960 A1 | 6/2004 | Demond et al. |
| 2003/0163064 A1 | 8/2003 | Vrba et al. | | 2004/0122466 A1 | 6/2004 | Bales |
| 2003/0171770 A1 | 9/2003 | Kusleika et al. | | 2004/0127933 A1 | 7/2004 | Demond et al. |
| 2003/0171771 A1 | 9/2003 | Anderson et al. | | 2004/0127934 A1 | 7/2004 | Gilson et al. |
| 2003/0171803 A1 | 9/2003 | Shimon | | 2004/0127936 A1 | 7/2004 | Salahieh et al. |
| 2003/0176884 A1 | 9/2003 | Berrada et al. | | 2004/0138693 A1 | 7/2004 | Eskuri et al. |
| 2003/0176885 A1 | 9/2003 | Broome et al. | | 2004/0138694 A1 | 7/2004 | Tran et al. |

| | | |
|---|---|---|
| 2004/0138696 A1 | 7/2004 | Drasler et al. |
| 2004/0144689 A1 | 7/2004 | Brady et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boylan et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225321 A1 | 11/2004 | Krolik et al. |
| 2004/0225322 A1 | 11/2004 | Garrison et al. |
| 2004/0236368 A1 | 11/2004 | McGuckin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Steeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahich |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salahieh et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |

| | | | |
|---|---|---|---|
| 2006/0206139 A1 | 9/2006 | Tekulve | |

FOREIGN PATENT DOCUMENTS

| | | |
|---|---|---|
| EP | 0 472 334 A1 | 2/1992 |
| EP | 0533511 A1 | 3/1993 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/45592 | 6/2001 |
| WO | WO01/87183 | 11/2001 |

* cited by examiner

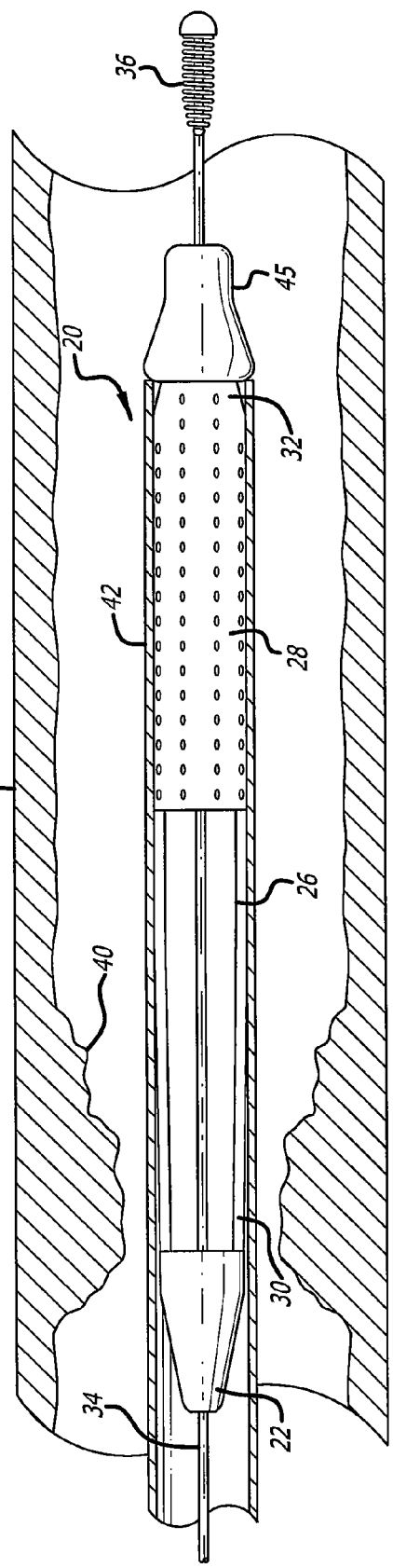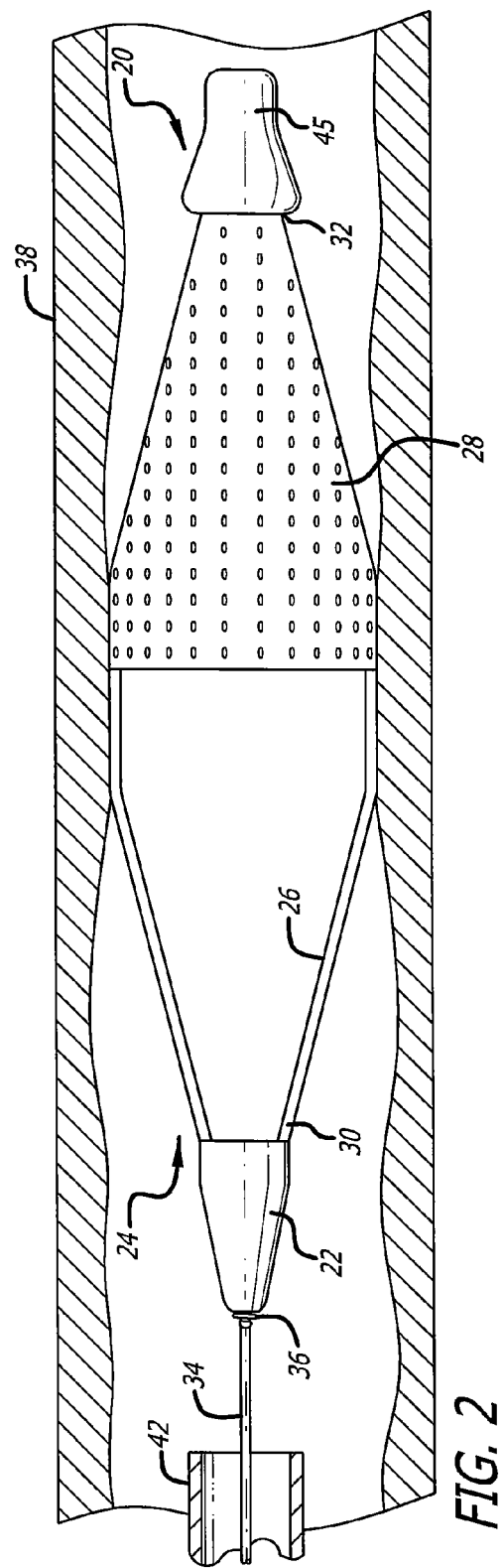

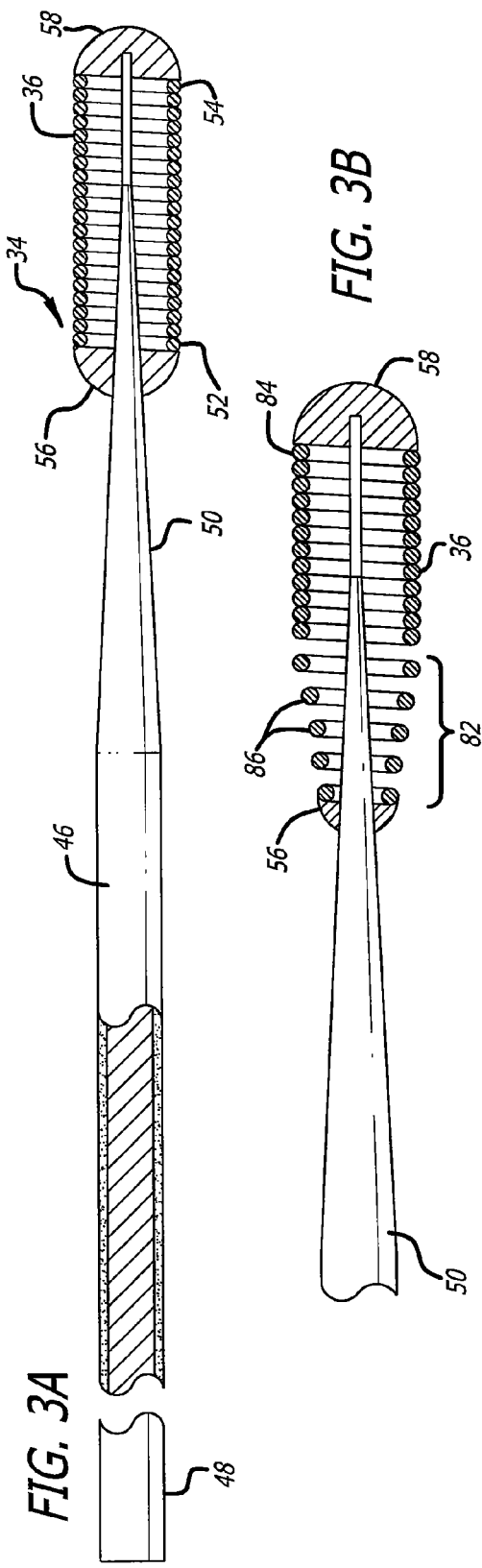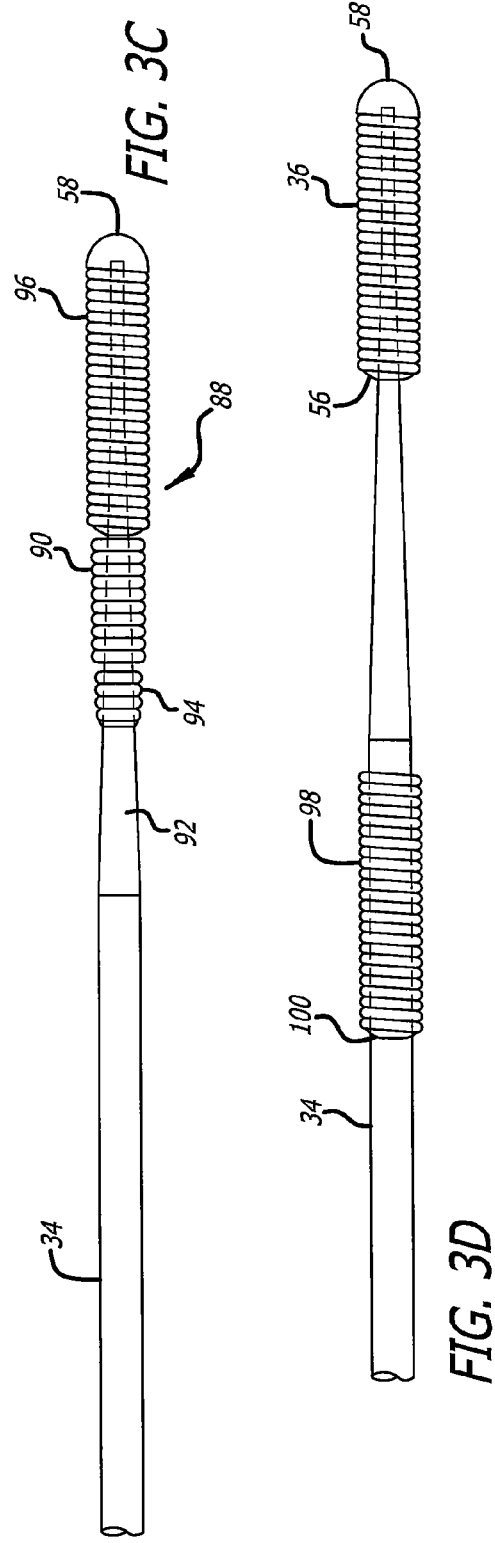

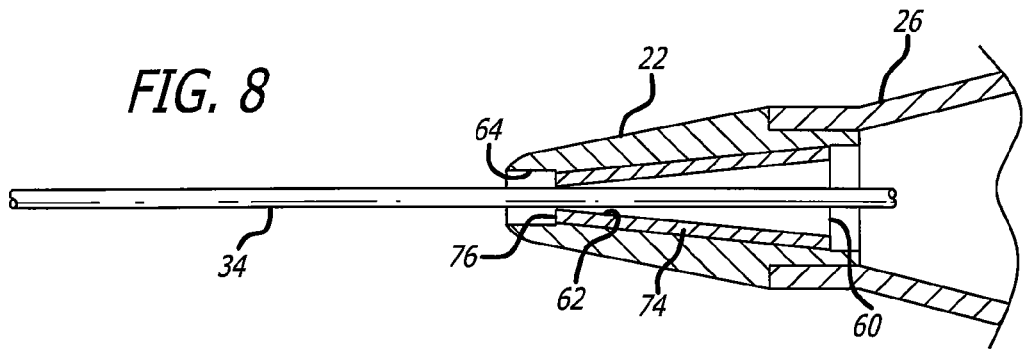
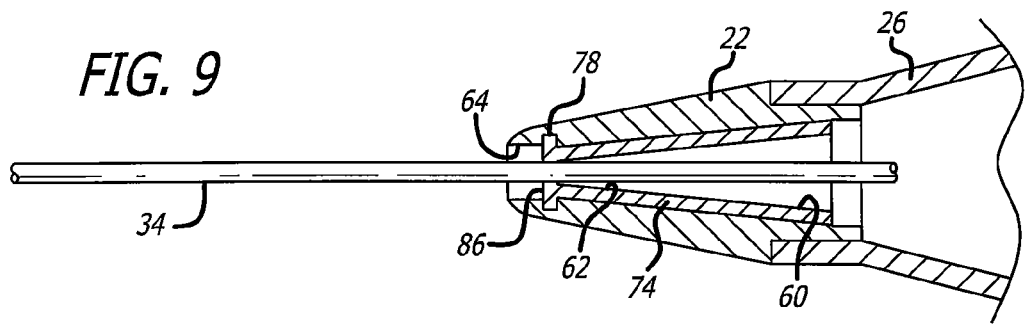

COMPONENT FOR DELIVERING AND LOCKING A MEDICAL DEVICE TO A GUIDE WIRE

BACKGROUND OF THE INVENTION

The present invention relates generally to medical devices used to perform interventional procedures in a patient's vasculature which can be delivered through the vasculature via a steerable guide wire that has been pre-deployed into an area of treatment, for example, a stenosed or occluded region of an artery or other body vessel. The present invention is more particularly directed to a locking component that can be attached to a medical device, such as embolic filter assembly used to capture embolic material that may be created and released into the vasculature during a stenting or angioplasty procedure, to allow the medical device to be delivered along the guide wire to the target area and locked into place. The locking component of the present invention can be in conjunction with conventional, readily-available guide wires or specially-designed guide wires which facilitate the locking features of the present invention.

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and create particles of plaque that can travel downstream and lodge somewhere in the patient's vascular system. Pieces of plaque material are sometimes generated during a balloon angioplasty procedure and are released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the vacuum catheter and, as a result, may enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, as mentioned above, there can be complications associated with such systems if the catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters vessel are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire or rapid exchange (RX) techniques to collapse the expanded filter for removal from the patient's vasculature.

Some prior art filtering devices utilize a construction in which the expandable filter is permanently affixed to the guide wire. When the expandable filter is permanently attached to the guide wire, the device may have added stiffness and therefore may lose some "front-line" capability, which is the ability to negotiate the often tortuous anatomy through which it is being delivered. The stiffness of a combined expandable filter and guide wire may possibly prevent the device from reaching the desired target area within the patient's vasculature. Also, in such a design, it is possible for the deployed filtering portion of the device to rotate or move with the guide wire in the event that the guide wire is rotated by the physician during usage. As a result, there is a possibility that the deployed filtering portion of the device could scrape the vessel wall possibly causing trauma. Therefore, when such a filtering device is utilized, it is important that the proximal end of the guide wire remains fixed since rotation could possible be transmitted to the deployed filtering portion of the device. However, since a physician normally delivers interventional devices along the guide wire after the filter portion has been deployed, some manipulation of the guide wire takes place an it may be difficult to prevent at least some rotation at the proximal end of the guide wire.

Some prior art filtering devices utilize a separate filtering assembly which can be delivered over the guide wire and attaches to a special fitting located near the distal end of the guide wire. However, these filtration devices require the fitting to be placed near the distal end of the guide wire which can possibly affect the ability to steer the guide wire and reach the target area in the patient's vasculature. These particular filter systems also require additional manufacturing procedures to properly mount the fitting onto the steerable guide wire. As such, the presence of the fitting near the distal end of the guide wire may cause unwanted problems during delivery of the guide wire through the patient's vasculature.

Therefore, what has been needed is a medical device that can be delivered and locked to a guide wire after the guide wire has been initially deployed into the target region of a patient. In particular, there is a need for a filtering device that is easy to deliver, easily attachable to the guide wire and possibly eliminates the need for special fittings to be placed on the guide wire. Also, it would be beneficial if the filtering device can be rotatably mounted onto the guide wire to prevent the deployed filtering device from rotating and possible scraping the vessel wall once deployed. The present invention satisfies these and other needs.

SUMMARY OF THE INVENTION

The present invention relates to a locking component for delivering and locking a medical device, such as an embolic filtering assembly used to capture embolic material that may be created and released into a patient's vasculature during a stenting or angioplasty procedure, along a pre-deployed guide wire. The locking component of the present invention can be used in conjunction with conventional, readily available guide wires or specially-designed guide wires which facilitate the locking features of the present invention. The locking component of the present invention is designed to slide over an elongate guide wire and lock onto a flexible and resilient body member, for example, a helical coil or a polymeric tubular member disposed on or around a portion of the guide wire. The locking component includes means for temporarily compressing at least a portion of the flexible body member (i.e., the coils) of the guide wire when the locking component is advanced over the flexible body member. The locking component further includes a recess which receives the compressed portion of the flexible body member. When the force which compresses the portion of the coil is removed, the resiliency of the formally compressed coils causes them to spring back to their original size within this recess. Once back to their original size, one or more of the coils now placed in the recess will abut against a shoulder or edge formed in the recess locking the locking component in place on the guide wire.

In one aspect of the invention, for example, when the flexible body member is a helical coil or other springy component, the coupling of the locking component to the helical coil creates a shock absorbing feature which helps to prevent the transmission of unwanted vibration or forces to the attached medical device. In this fashion, the coupling of the locking component to the coils of the guide wire utilizes the springiness and resiliency of the coils to provide shock-absorbing capabilities.

In one particular aspect of the present invention, the locking component is made from a body member having a longitudinal opening which extends through the body member and is adapted to receive and temporarily compress at least a portion of the flexible body member (the coil, for example). This longitudinal opening can be tapered from a large diameter to a smaller diameter, which causes the temporary compression of the helical coil as the coil moves through the tapered opening. The locking recess formed in the body member can be located adjacent to, and in communication with, the smallest diameter of this tapered longitudinal opening. Accordingly, this smallest diameter of the tapered opening produces the most compression to the portion of the coil which passes through it. As such, as the coil of the guide wire is compressed and stretched through this smallest diameter, the compressed portion of the coil moves into the larger locking recess which is located adjacent to the small diameter opening. Ultimately, depending upon the coil stretch and length, the portion of the coil which remains distal to the small diameter opening become somewhat stacked, thus preventing any further forward movement of the locking component along the length of the coil. When forward pressure is released, the portion of the coil that has passed into the locking recess will return back to their original size (diameter) thus restricting the locking component from further movement since this portion of the coil are too large to pass back through the smaller diameter opening through which they passed. Therefore, the locking component, and attached medical device, will remain locked to the guide wire.

Generally, the smallest diameter of this tapered opening should be smaller than the normal diameter of the helical coil formed on the guide wire. The larger diameter opening should be sufficiently large to receive the coil. The tapered opening will then gradually compress a portion of the length of coil as the locking component advances over the coil.

The locking component of the present invention allows the physician to use or deploy a medical device, such as a distal embolic filtering device, at any point during an interventional procedure without the need to remove a previously deployed guide wire and re-cross the lesion with an entirely separate distal embolic filtering device. Thus, the present invention allows the physician to initially use a conventional guide wire, which performs like a standard guide wire, while providing the physician the option to implement embolic distal protection at any time during the interventional procedure.

There are multiple possible configurations for the locking component which can be manufactured in accordance with the present invention. For example, the body member which forms the locking component can be tubular, cylindrical, or bullet shaped, just to mention a few configurations. Generally however, the body member of the locking component should usually have a sleek, low-profile shape to minimize possible trauma to the vessel walls of the patient's vasculature especially when the locking component is placed, for example, on the distal end of an embolic filtering assembly. The size and shape of the locking component also should reduce the overall profile of the delivery system in order to reach tight distal locations in the patient's vasculature.

In one particular aspect, the present invention provides a separately deliverable filter assembly having an expandable basket (also referred to as a "cage") and a filter element that can be attached to the distal coil tip of a conventional guide wire. In use, the present invention is designed to capture embolic debris created during the performance of a therapeutic interventional procedure, such as a balloon angioplasty or stenting procedure, or other unwanted particulates entrained in the fluid of a body vessel. The present invention allows the physician to deliver the guide wire with "front-line" capabilities to steer through the tortuous anatomy, while still being able to provide filtering protection in the form of a separately deliverable attachment.

An embolic filtering device made in accordance with the present invention utilizes a filter assembly having an expandable basket capable of being disposed for traveling along a deployed guide wire. The filter assembly has a proximal end and a distal end with a guide wire locking component coupled to either the distal end or proximal end. Once in proper position, the guide wire locking component is able to be coupled to the distal tip coil of the guide wire. The expandable basket can be made from a self-expanding material, for example, nickel-titanium alloy (NiTi), and may include struts capable of expanding from a collapsed position or configuration having a first delivery diameter to an expanded or deployed position or configuration having a second implanted diameter. The filter element may be made from an embolic-capturing material and is attached to the expandable basket such that it moves with the basket between the collapsed and deployed positions. Guide wire locking components of the present invention are easily adapted for attachment on a number of different configurations of filter assemblies and can be attached to a variety of different guide wires.

The guide wire used in the present invention may include steerable guide wires having distal tip coils which allow the guide wire locking component to be locked onto the tip coil. Also, any guide wire with a coil tip which has a sufficient outer diameter to allow the guide wire locking component to properly engage the tip coil may be implemented. Another guide wire that may be used in the present invention is found in U.S. Pat. No. 6,132,389 issued to Cornish et al., which discloses a proximally tapered guide wire tip coil.

In one particular embodiment of the present invention, the locking component can be used with a specially-designed guide wire which includes a flexible body member located at a position along the length of the guide wire proximal to the distal end coil of the guide wire. Additionally, another specially designed guide wire which can be used with the present invention includes a coil which is rotatably mounted to the guide wire to allow the locking component and attached medical device to spin somewhat freely relative to the guide wire.

In use, the present invention is able to capture embolic debris or other particulates entrained in the fluid of a blood vessel of a patient during, for example, an interventional procedure such as an angioplasty procedure or stenting procedure. Initially, a guide wire having a distal tip coil would be inserted into the body vessel and steered into the target area. Once the guide wire is delivered across the area of treatment the filter assembly, which has a guide wire locking component attached to either the distal or proximal end of the filter assembly, would be delivered along the guide wire until it reaches the distal end of the guide wire. The guide wire locking component would then be moved over to the tip coil of the guide wire.

In order to transfer the filter assembly along the guide wire, the expandable basket of the filter assembly would be maintained in a collapsed position by a delivery sheath, or other delivery catheter, which extends co-axially over the filter assembly. Alternatively, a rapid exchange delivery sheath could be used in which an offset lumen is utilized to maintain the filter assembly in a collapsed position. The delivery sheath, along with the collapsed filter assembly, can be delivered over the guide wire until the guide wire locking component of the filter assembly locks the filter assembly to the guide wire. The filter assembly can be placed in its expanded position simply by retracting the delivery sheath proximally, allowing the expandable basket to self deploy. As the struts of the basket expand radially, so does the filter element which will now be deployed within the body vessel to collect embolic debris and particles that may be released into the bloodstream as the physician performs the interventional procedure. The delivery sheath can be removed from the guide wire to allow an interventional device to be delivered over the guide wire to the area of treatment. After the procedure is completed, the interventional device is removed from the guide wire and a recovery sheath can be delivered along the guide wire and over the filter assembly to return it to its collapsed position. The guide wire, along with the recovery sheath and filter assembly, can be then removed from the patient.

It is to be understood that the present invention is not limited by the embodiments described herein. Alternatively, the present invention can be used in arteries, veins, and other body vessels. By altering the size of this design, the present invention would be suitable for coronary, peripheral and neurological applications. Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in cross-section, of a guide wire with an embolic filter assembly with guide wire locking component embodying features of the present invention being delivered into a body lumen.

FIG. 2 is an elevational view of the embodiment of a filter assembly and guide wire locking component of FIG. 1 deployed within the body lumen.

FIG. 3A is an elevational view, partially in cross section, of a conventional guide wire with distal tip coil, which can be used with the present invention.

FIG. 3B is an elevational view, partially in cross section, of the distal end portion of a guide wire having a proximally tapered, partially stretched tip coil, which can be used with the present invention.

FIG. 3C is an elevational view, partially in cross section, of the distal end portion of a guide wire which includes a rotating coil section which forms a portion of the distal tip coil of the guide wire.

FIG. 3D is an elevational view, partially in cross section, of the distal end portion of a guide wire which includes a flexible body member, such as a coil section, disposed along a length of the guide wire proximal to the distal tip coil of the guide wire.

FIG. 8 is an elevational view, partially in cross-section, of an alternative embodiment of the guide wire locking component disposed on a guide wire.

FIG. 9 is an elevational view, partially in cross-section, of an alternative embodiment of the guide wire locking component disposed on a guide wire.

DETAILED DESCRIPTION OF THE PREFERRED EMBODIMENTS

Figure 4:
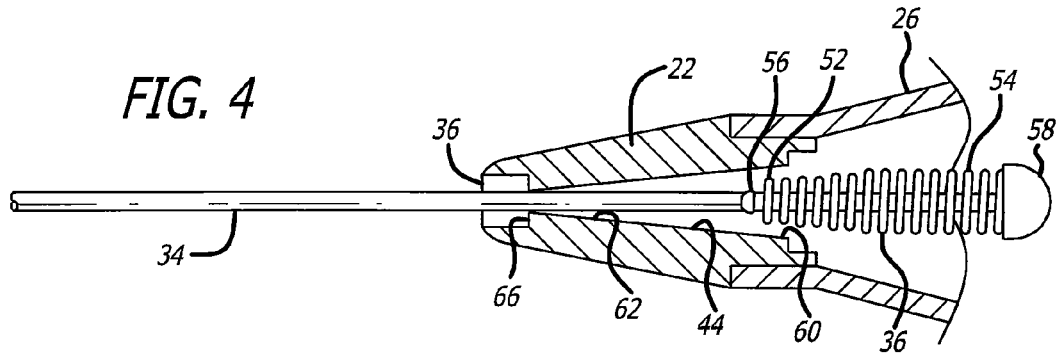
FIGS. 4-6 are elevational views, partially in cross-section, exemplifying the states of locking deployment of an embodiment of the guide wire locking component made in accordance with the present invention on a conventional guide wire.

The present invention relates to a locking component used to deliver and lock a medical device along a pre-deployed guide wire. For the sake of illustration, the following exemplary embodiments are directed to locking components which are attached to embolic filtering devices, although it is understood that the present invention is applicable for use with other medical devices that can be delivered in over-the-wire fashion and locked to a guide wire that has been pre-deployed in a body lumen, such as an artery, vein and other body vessel. By altering the size of the components, the present invention can be suitable for coronary, peripheral and neurological applications. It is to be understood that the present invention is not limited by the embodiments described therein.

Turning now to the drawings, in which like reference numerals represent like or corresponding elements in the drawings, FIGS. 1 and 2 illustrate one particular embodiment of an embolic filtering device 20, which is attached to a guide wire locking component 22 incorporating features of the present invention. This embolic filtering device 20 is designed to capture, for example, embolic debris which may be created and released into a body vessel during an interventional procedure. The embolic filtering device also can be used to filter any unwanted particles entrained in the fluid of a body vessel, such as large microspheres of a therapeutic agent which may be released into the vessel during a localized drug delivery procedure.

The embolic filtering device 20 includes an expandable filter assembly 24 having a self-expanding basket or cage 26 and a filter element 28 attached thereto. The filter assembly 24 has a proximal or first end 30 and a distal or second end 32, and in the embodiment shown in FIG. 1, the guide wire locking component 22 is shown attached to the proximal end 30 of the filter assembly 24. In FIGS. 1 and 2, the expandable filter assembly 24 is engaged with an elongated (solid or hollow) cylindrical tubular shaft, such as a steerable guide wire 34 having a distal tip coil 36. The guide wire 34 has a proximal end (not shown in FIGS. 1 and 2) which extends outside the patient.

In FIGS. 1 and 2, the embolic filtering device 20 is shown within an artery 38 or other body vessel of the patient. A portion of the artery 38 has an area which needs treatment, for example, atherosclerotic plaque (stenosis) 40 that has built up against the inside wall of the artery 38. In operation, the physician would first insert the guide wire 34 into the vasculature of the patient, positioning the distal end 36 of the guide wire 34 past the area of treatment. This guide wire 34 is delivered and steered by the physician using techniques well known in the medical profession. The physician can now deliver an interventional device along the deployed guide wire to treat the stenosis 40, or can first deploy an embolic filtering device past the stenosis 40 to catch possible particles which could break from the stenosis during treatment. If the physician decides to opt for distal embolic protection, a restraining or delivery sheath 42 that delivers the filter assembly 24 separately along the guide wire 34 in a collapsed position can be delivered along the guide wire and downstream from the lesion.

In the particular embodiment shown in FIGS. 1 and 2, the physician advances the delivery sheath 42 and filter assembly 24 along the guide wire 34 to allow the guide wire locking component 22 to reach the flexible body member 36 disposed on the guide wire, such as the tip coil 36. As the sheath 42 and filter assembly 24 are advanced over the guide wire, the distal tip coil 36 eventually enters into a tapered opening 44 (See FIG. 4) which extends through the guide wire locking component 22. As the guide wire locking component 22 is advanced over the tip coil 36, it will eventually lock in place, as will be described in further detail below. Then, once connected to the guide wire 34, the expandable filter assembly 24 can be deployed by the physician by simply retracting the delivery sheath 42 proximally to expose the expandable filter assembly 24. Once the restraining sheath 42 is retracted, the self-expanding basket 26 immediately begins to expand within the body vessel 38, causing the filter element 28 to expand as well. By attaching the filter assembly 22 to the guide wire after the guide wire has been delivered to the area of treatment, the physician is able to deliver the guide wire with "front-line" capabilities and is still able to obtain embolic protection as a separate attachment.

As can be seen in FIGS. 1 and 2, the filter assembly 24 may include an obturator 45 made from a soft material such as PEBAX 40D which provides an atraumatic tip to the filter assembly as it is being advanced over the guide wire within the patient's vasculature. The soft-tipped obturator 45 helps to prevent the distal end of the filter from scraping the walls of the body vessel as it is being advanced therethrough. This same type of obturator can be used to in accordance with any of the other embodiments of the filter assembly used in accordance with the present invention Referring specifically now to FIG. 2, the embolic filtering device 20 is shown in its expanded position within the patient's artery 38. A treatment device (not shown), such as an angioplasty catheter or stent-bearing catheter can be delivered over the guide wire 34 to the area of plaque stenosis for treatment. Any embolic debris created during an interventional procedure will be released into the bloodstream and will enter the filter assembly 34 located downstream from the area of treatment. Once the procedure is completed and the embolic debris is collected in the filter element 28, the filter assembly can be collapsed by a recovery sheath (not shown) which slides over the filter assembly, allowing the embolic filter device to be removed from the patient's vasculature.

The guide wire locking component 22 can be utilized with a conventional guide wire 34 having a flexible body member 36, i.e. a coil, which is usually disposed at a distal end and used for initially steering the guide wire through the sometimes tortuous path to the area of treatment. Referring now to FIG. 3A, a representation of a conventional guide wire 34 is shown. The guide wire 34 depicted in FIG. 3A includes an elongate core member 46 with a proximal section 48 and a distal section 50. A flexible body member 36 or helical coil is disposed around the distal section 50, and the helical coil 36 has a proximal end 52 and a distal end 54. In this embodiment, the helical coil 36 has a relatively constant diameter from the proximal end 52 to the distal end 54. The helical coil 36 can be attached to the guide wire 34 at the proximal end 52 by a solder joint 56. The distal end 54 also has a rounded solder joint 58 as well. In the event that the spacing between coils is too tight, i.e., the tip is too stiff and will not bend through tortuous anatomy, the physician can simply apply a small amount of proximal force to the coils to cause a portion of the tip coil to expand longitudinally, thus creating space between coils which should enhance the ability of the locking component 22 to catch and hold onto the tip coil.

Figure 5:
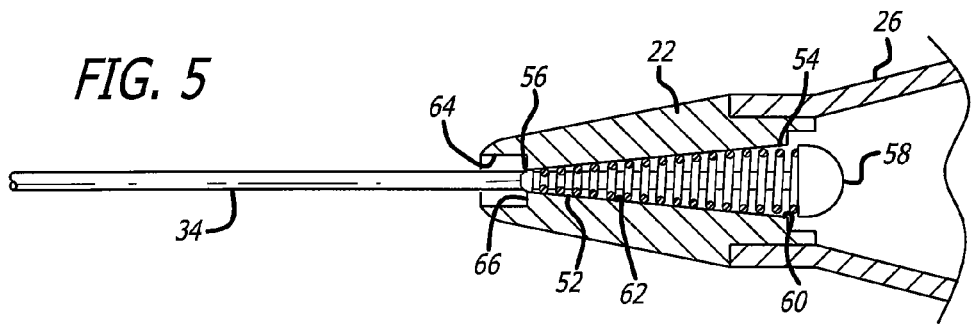
Figure 6:
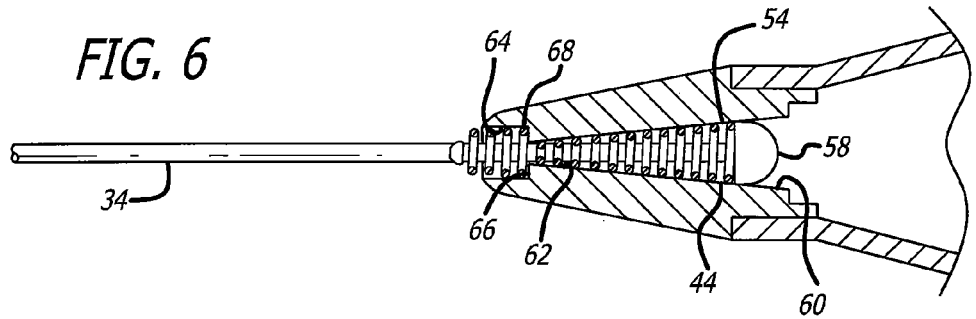

Referring now to FIGS. 4-6, one particular embodiment of a guide wire locking component 22 made in accordance with the present invention is shown exemplifying the various states of locking deployment that the locking component 22 takes when being advanced over the distal coil 36 of a conventional guide wire 34. As can be seen specifically in FIG. 4, the locking component 22 includes the longitudinal opening 44 which in this particular embodiment is shown as a proximally tapered opening. In this regard, the longitudinal opening 44 includes a distal entry opening 60 which forms the largest diameter of the tapered opening. The proximally tapered opening 44 extends along the length of the body member of the locking component to a smaller exit opening 62 which defines the smallest diameter of the tapered opening 44. Immediately adjacent to this exit opening 62 is a locking recess 64 which has a diameter that is larger than the diameter of this exit opening 62. The recess 64 forms an abutting shoulder or edge 66 which, as explained before, is utilized in order to lock the component 22 onto the coil 36. The size of this locking recess 64 should be large enough to allow the portion of the coil which enters into it to spring back to its original diameter once advancement of the locking component over the coil has stopped.

Referring now to FIGS. 5 and 6, the locking component 22 is shown as it is advanced over the distal helical coil 36 of the guide wire 34. In this regard, the proximal end 52 of the coil 36 is shown near the exit opening 62 of the tapered opening 44. As the locking component 22 is moved along this coil 36, the proximal end 52 of the coil 36 begins to stretch somewhat and compress to a diameter which is smaller than the diameter of the coil in its normal uncompressed position, which is shown in FIG. 4. This compression of the proximal end 52 of the coil 36 is achieved by the configuration of this proximally tapered opening 44. Referring specifically now to FIG. 6, as the locking component 22 is further advanced along the coil in a distal direction, some of the individual coils at the proximal end 52 of the coil 36 begin to extend into the locking recess 64. Additionally, mid-coils and coils located at the distal end 54 of the coil 36 begin to bunch up which causes a stoppage of any further advancement of the locking component 22 over the coil 36. When movement is halted, the individual coils at the proximal end of the composite coil 36 which were temporarily compressed, as shown in FIG. 5, will resiliently expand back to their normal shape within the larger diameter opening of the locking recess 64. As a result, one or more of the individual coils 68 will abut against the shoulder or edge 66 formed in the recess 64. In this manner, the locking component 22 remains locked in place on this distal coil 36 and will remain locked on the coil until the entire guide wire 34, with attached embolic assembly 24, is to be removed from the body lumen.

When a distal coil or another coil is utilized as the component onto which the locking component 22 is locked, the amount of coil stretch and the length of coil which extends into the recess 64 can, of course, vary. Generally, the proximal solder joint 56 should have a diameter which is smaller than the diameter of the exit opening 62. As the solder joint 56 passes through the exit opening 62, a slight interference between this small diameter and the joint 56 may result. In this regard, the locking component may be made from a material which possesses some flexibility to allow the exit opening 62 to stretch somewhat as the solder joint 56 passes through the opening. However, the material used to form the body of the locking component 22 should have sufficient rigidity at the abutting shoulder or edge 66 so as to prevent the expanded coil 68 from moving back into the opening 62. Otherwise, the locking component 22 may not adequately lock in place.

Figure 7:
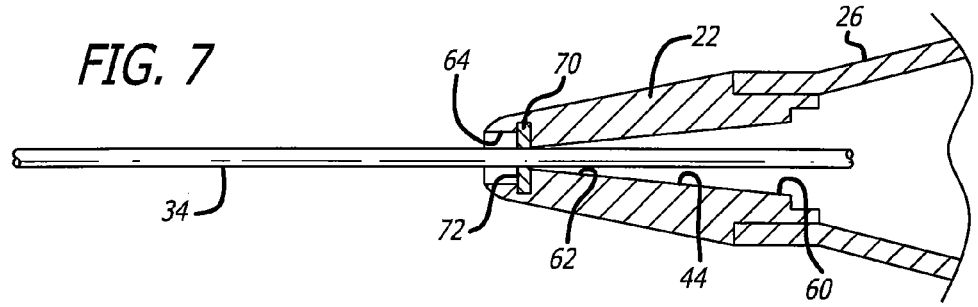
FIG. 7 is an elevational view, partially in cross-section, of an alternative embodiment of the guide wire locking component disposed on a guide wire.

Referring now specifically to FIG. 7, an alternative design of the locking component 22 includes the tapered longitudinal opening 44 with entry opening 60 and exit opening 62. The recess 64 further includes a ring member 70 formed into the body of the locking component 22 to provide additional stiffness which may be necessary to maintain the coil locked in place. In this regard, the ring member 70 includes an edge 72 which acts like the abutting shoulder. This particular arrangement of components allows the body of the locking component to be made from a soft material, such as Pellethane 55D, since the ring member 70 could be made from metal or any one of a number of different stiff materials, such as stainless steel, nickel-titanium alloy, polymeric materials such as polyimide, just to name a few, which would provide a hard surface which helps to retain the coil. Additionally, the ring member 70 could be made from a platinum material or other highly radiopaque material which additionally provides a locating marker for the physician when using visualization equipment such as a fluoroscope to visualize and position the locking component and filter assembly in the patient's vasculature.

The locking system of the present invention also results in the embolic filtering assembly being locked onto a natural shock absorber (the coil 36) once locked into place. The actual location where the locking component 22 will lock is dependent upon the length of stretch and the amount of stretch of the coil. However, once locked, the locking component will have stretched coils on either side of the locking recess. This arrangement of stretched coils acts somewhat like a shock absorber, in that the embolic filtering assembly is able to spring forward and backward some distance relative to the guide wire.

Referring now to FIGS. 8 and 9, alternative embodiments of a locking component 22 are shown. Referring initially to FIG. 8, the locking component 22 is shown including a longitudinally tapered opening 44 created by a tapered tubing 74 made from a metal or hard polymeric material. This tapered tubing allows the remaining body of the locking component 22 to be made from a softer material such as Pellethane 55D. This tapered tubing 74 includes a larger diameter entry opening 60 with a smaller exit opening 62. The edge 76 of the tapered tubing 74 acts somewhat like the abutting shoulder in this particular embodiment to prevent the proximate end of the coil 36 from moving from the locking recess 64 once locked into place. Suitable materials for this tapered tubing 74 include stainless steel, nickel-titanium alloys, platinum alloys, polymeric materials such as polyimide, and the like. Other suitable materials include platinum and other highly radiopaque material which additionally provides a locating marker for the physician when using visualization equipment such as a fluoroscope to visualize and position the locking component and filter assembly in the patient's vasculature. In this regard, the tapered tubing 74 provides a hard contact surface which helps to facilitate the compression of the proximal coils 36 as they advance through the proximally tapered opening 44.

In the embodiment of the locking component 22 shown in FIG. 9, the tapered tubing 74 includes a flanged portion 78 which extends into the recess 64 formed on the body of the locking component. This flange 78 provides a hard abutting shoulder 80 which, again, helps to prevent the proximal coils from escaping from within recess 64. This particular tapered tubing 74 and flange 76 can be manufactured as a single piece or as two separate pieces attached together using soldering, welding and other well-known bonding techniques for attaching such components together.

Figure 10:
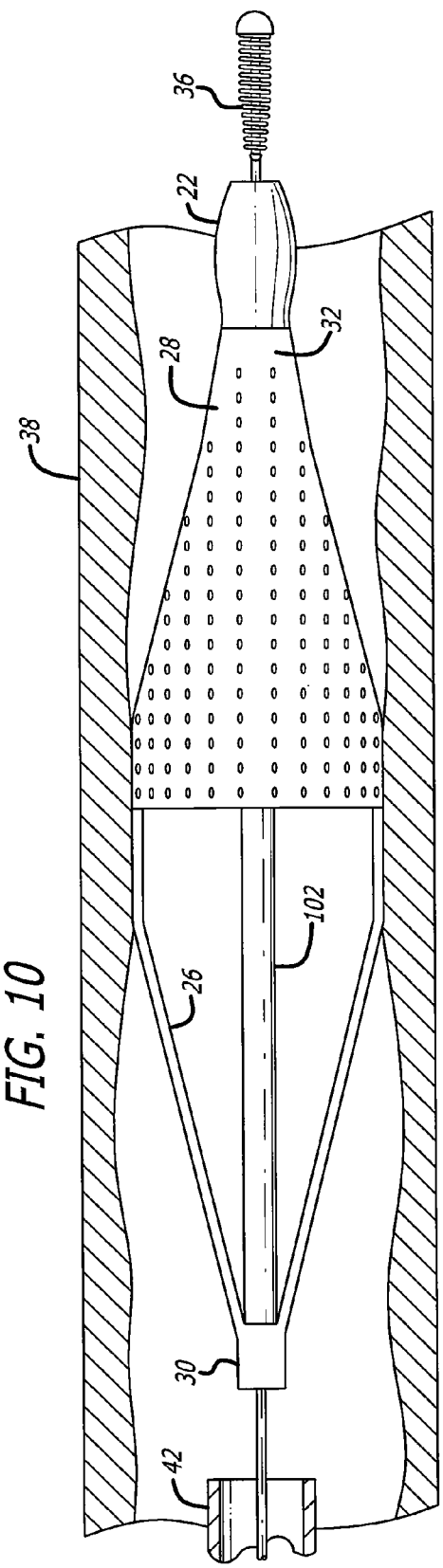
FIG. 10 is an elevational view, partially in cross-section, of another embodiment of the guide wire locking component coupled to the distal end of a filter assembly.
Figure 11:
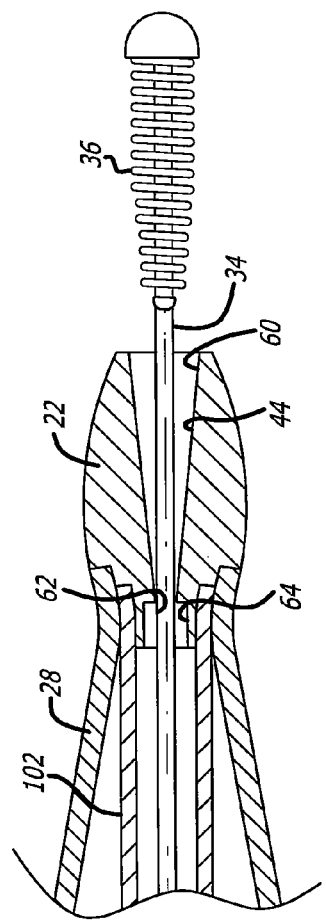
FIG. 11 is an elevational view, partially in cross-section, of the guide wire locking component of FIG. 10, showing the distal attachment of the component to the filter assembly.

Referring now to FIGS. 10 and 11, the locking component 22 is shown attached to the distal end 32 of the filter assembly. In this regard, the structure of the locking component is substantially similar to that shown in the previous embodiment, except that the locking component 22 is adapted to act like an obturator 45 as well. The distal end 32 of the embolic filtering assembly 24 can be bonded or attached to the locking component 22 using any one of numerous known techniques in the art.

Another embodiment of a guide wire 34 that can be utilized with the present invention, which includes a helical coil having a tapered proximal end, is shown in FIG. 3B. This particular guide wire 34 is very similar to the proximally tapered coil described in U.S. Pat. No. 6,132,389 issued to Cornish et al. As is shown in FIG. 3B, the proximal end 82 of the coil 36 is at an angle with the longitudinal axis of the helical coil. This angle can be from about 0.1 to 10° and preferably about 0.5 to 2°. The distal end 84 of the helical coil typically has an outer diameter approximately equal to the nominal outer diameter of the proximal section of the elongate core member. The tapered proximal end shown in FIG. 3B differs somewhat from the proximal tapered helical coil found in the Cornish et al. patent in that the tapered proximal end is somewhat stretched, forming spaces or gaps in between individual coils. The increased gap 86 between adjacent coils may help to enhance the ability of the shoulder of the recess to abut against the coil(s) to maintain the locking component in a locked position.

Referring now to FIG. 3C, another embodiment of a specially adapted guide wire is shown. In this particular embodiment, the guide wire 34 has a composite tip coil 88 including a rotating coil section 90 which is rotatably mounted to the core 92 of the guide wire. This rotating coil section 90 is disposed between a proximal coil section 94 and a distal coil section 96 which are both fixed to the core 92 of the guide wire. The proximal coil section 94 and the distal coil section 96 act as stop fittings to maintain the rotating coil segment 90 longitudinally fixed there between, yet allows the rotating coil segment 90 to rotate relative to the guide wire. The proximal coil section and distal coil section, along with the rotating coil section, cooperatively form a composite tip coil which can be bent to a J-shaped configuration, or other configuration, as is well-known in the art, to aid in the steering of the guide wire through the patient's anatomy.

The guide wire locking component 22 is adapted to engage and attach to the rotating coil section 90 which forms the composite tip coil. It should be appreciated that the outer diameter of the proximal coil section 94 may be somewhat smaller than the outer diameter of the rotating coil section 90 to allow locking component to be advanced over the composite tip coil.

Referring now to FIG. 3D, yet another guide wire 34 which can be used in conjunction with the present invention is shown. This particular embodiment of the guide wire 34 is disclosed in order to show that the locking component 22 can be adapted to lock on various types of flexible body members which are associated with the guide wire, not necessarily the distal tip coil found on most conventional guide wires. In this regard, the flexible body member 96 to which the locking component 22 is to be coupled is shown located proximal to the distal coil tip 36. This flexible body member 96 is shown as a helical coil which is attached to the core of the guide wire via a solder joint 100. The locking component 22 would be advance over this flexible body member 98 in the same fashion as is shown in FIGS. 4-6 and described above. While this flexible body member 96 is again shown as a flexible coil, it is to be understood that other forms of a flexible body member could be utilized in accordance with the present invention. A helical coil is a preferred form of the flexible body member since it possesses sufficient resiliency to be compressed via the advancement through the tapered opening of the locking component while possessing sufficient resiliency to spring back to its original shape (diameter) once placed in the locking recess formed in the locking component. While the coil is generally shown as being made from a circular wire, it is to be understood that other cross-sectional wires could be utilized as well. Additionally, the flexible body member could be simply a resilient fitting made from a material which has the necessary properties of being temporarily compressed but capable of springing back to its original size, or near original size, once it reaches the locking recess.

It should be appreciated that the guide wire locking assembly can be a separate piece which is bonded or otherwise attached to any conventional filtering assembly. Accordingly, the guide wire locking component 22 can take on many different shapes and forms other than those shown in the particular figures disclosed herein to perform the same function as that disclosed herein. It should be appreciated that modifications can be made to the guide wire, filter assembly and guide wire locking component without departing from the spirit and scope of the present invention.

When the filtering assembly 24 is collapsed by the recovery sheath, there is a possibility that the proximal end of the filter assembly may move somewhat distally as the end of the recovery sheath contacts the assembly. This may occur, for example, in the embodiment shown in FIGS. 10 and 11, since the proximal end of the filter assembly is not physically attached to the guide wire, but rather is slidably disposed on the guide wire. This may not occur if the expandable basket has sufficient axial stiffness. However, when a filter assembly such as the one in FIG. 9 is utilized, a recovery sheath having a large inner diameter may be used to capture a greater portion of the proximal end of the filter assembly. As a result, the recovery sheath may help to prevent the proximal end from moving distally as the sheath slides over the filter assembly. Another way to prevent the proximal end from moving is to utilize a tubular member 102 or shaft, such as is shown in the embodiments of FIGS. 10 and 11. The tubular shaft 102 provides axial rigidity which prevents the proximal end of the filter assembly from being pushed distally as a recovery sheath extends over the filter assembly. The tubular shaft 102 used in accordance with the embodiments of FIGS. 10 and 11 is just one example of adding stiffness in a longitudinal direction to enhance the ability of the filter assembly to be collapsed by the recovery sheath.

The guide wire locking component can take on many different shapes and forms other than those shown in the particular figures disclosed herein to perform the same, or virtually the same function as that described herein. Generally, the locking component can be made in a number of different ways, including injection molding, heat shrink molding, or it can be machined from a metallic or plastic material. As mentioned above, a soft material such as Pellethane 55D could be used as well. The tapered opening may be part of the molded or machined device or may be a separate material for improving a feature such as radiopacity. The dimensions and specs can be varied to meet almost any design criteria. For coronary and other procedures which typically use a 0.014 diameter guide wire, the maximum coil outer diameter should be about 0.0138 inches. The smallest diameter of the tapered opening would be approximately 0.0125 to 0.0130 inches. The proximal guide wire core would be about 0.012 inches or the maximum diameter that would fit into the tapered opening. It should be appreciated that modifications can be made to the guide wire, filter assembly and guide wire locking component without departing from the spirit and scope of the present invention.

The elongate core member which forms part of the guide wire is typically comprised of metal, preferably stainless steel or a nickel titanium alloy or a combination thereof, but can also consist of any material that yields the approximate mechanical properties of the named metals so long as the material is sufficiently biocompatible. Other materials, such as high strength alloys, may also be used for the core member, either alone, or in combination with other materials such as those previously mentioned. The proximal section of the core member and any portion of the core member not covered by the flexible body member may optionally be used with a lubricious coating such as a fluoropolymer, eg. Teflon® by DuPont. It may also be coated with a silicone based coating, such as Microglide™ coating used by the present assignee, Advanced Cardiovascular Systems, Inc. on many of its commercially available guide wires. Other similar coatings, for example, hydrophylic coatings, or a combination of any of the above mentioned coatings may also be used.

The flexible body member 36 can be disposed around all or part of the guide wire 34. The flexible body member can be comprised of many suitable materials that allow for increasing the diameter of the guidewire in the distal section without adding substantial stiffness to that section. Suitable materials include polymers, composites, and metals. Preferably the flexible body member is comprised of a helical shaped metallic coil, more preferably a metal or composition of metal or alloys with some degree of radiopacity in order to facilitate flouroscopic viewing of the device while in use. Metals suitable for the flexible body member may include gold, platinum, tantalum, stainless steel, and nickel titanium alloys, MP35N, or a combination or alloy of any of the foregoing. A flexible body member comprised of metallic helical coils is typically comprised of coil winding material that can have a cross sectional diameter of about 0.001 inches (0.025 mm) to about 0.008 inches (0.20 mm), preferably about 0.002 inches (0.05 mm) to about 0.004 inches (0.1 mm).

The expandable basket which can be used with the present invention can be made in many ways. One particular method of making the basket is to cut a thin-walled tubular member, such as nickel-titanium hypotube, to remove portions of the tubing in the desired pattern for each strut, leaving relatively untouched the portions of the tubing which form the structure. The tubing may be cut into the desired pattern by means of a machine-controlled laser. The tubing used to make the basket could possibly be made of suitable biocompatible material, such as spring steel. Elgiloy is another material which could possibly be used to manufacture the basket. Also, very elastic polymers possibly could be used to manufacture the basket. The expandable basket also could be made from a flexible wire, made from a material such as a nickel-titanium alloy, or specially processed nickel-titanium alloy, which is capable of expanding. Such a wire basket could be "set" to an expanded position which allows the basket to move from a collapsed position to the expanded position once the restraining sheath or other restraining means is removed from the basket.

The strut size is often very small, so the tubing from which the basket is made may have a small diameter. Typically, the tubing has an outer diameter on the order of about 0.020-0.040 inches in the unexpanded condition. Also, the basket can be cut from large diameter tubing. Fittings are attached to both ends of the lased tube to form the final basket geometry. The wall thickness of the tubing is usually about 0.076 mm (0.001-0.010 inches). As can be appreciated, the strut width and/or depth at the bending points will be less. For baskets deployed in body lumens, such as PTA applications, the dimensions of the tubing may be correspondingly larger. While it is preferred that the basket be made from laser cut tubing, those skilled in the art will realize that the basket can be laser cut from a flat sheet and then rolled up in a cylindrical configuration with the longitudinal edges welded to form a cylindrical member.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The basket can be laser cut much like a stent is laser cut. Details on how the tubing can be cut by a laser are found in U.S. Pat. Nos. 5,759,192 (Saunders), 5,780,807 (Saunders) and 6,131,266 (Saunders) which have been assigned to Advanced Cardiovascular Systems, Inc.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050-0.0050 inches. The wall thickness may vary depending on the particular material selected. The material can be made into a cone or similarly sized shape utilizing blow-mold technology or dip molding technology. The openings can be any different shape or size. A laser, a heated rod or other process can be utilized to create to perfusion openings in the filter material. The holes would, of course, be properly sized to catch the particular size of embolic debris of interest. Holes can be lazed in a spinal pattern with some similar pattern which will aid in the re-wrapping of the media during closure of the device. Additionally, the filter material can have a "set" put in it much like the "set" used in dilatation balloons to make the filter element re-wrap more easily when placed in the collapsed position.

The materials which can be utilized for the restraining sheath can be made from polymeric material such as cross-linked HDPE. This sheath can alternatively be made from a material such as polyolefin which has sufficient strength to hold the compressed strut assembly and has relatively low frictional characteristics to minimize any friction between the filter assembly and the sheath. Friction can be further reduced by applying a coat of silicone lubricant, such as Microglide®, to the inside surface of the restraining sheath before the sheath is placed over the filter assembly. Silicone also can be placed on the filter material as well.

Further modifications and improvements may additionally be made to the device and method disclosed herein without departing from the scope of the present invention. Accordingly, it is not intended that the invention be limited, except as by the appended claims.

What is claimed is:

1. A system for locking a component along a guide wire, comprising:
   a guide wire having a flexible body member disposed thereon;
   a locking component having a body member including means for temporarily compressing at least a portion of the flexible body member of the guide wire to allow the compressed portion of the flexible body member to be placed in a recess formed in the body member, the compressed portion of the flexible body member being adapted to decompress within the recess to lock the formerly compressed portion of the flexible body member within the recess; and
   a medical device which is deliverable over the guide wire and coupled to the locking component, wherein the flexible body member disposed on the guide wire is a coil spring.

2. The locking system of claim 1, wherein the means for temporarily compressing the flexible body member of the guide wire is a longitudinal opening extending into the body member which is adapted to receive and temporarily compress at least a portion of the flexible body member.

3. The locking system of claim 2, wherein the longitudinal opening extending into the body member is proximally tapered from one diameter to a smaller diameter.

4. The locking system of claim 3, wherein the recess formed in the locking device is adjacent to the smaller diameter of the longitudinal opening and in communication with the longitudinal opening.

5. The locking system of claim 4, further including a ring member disposed in the recess adjacent to the smaller diameter of the longitudinal opening.

6. The locking system of claim 5, wherein the ring member is made from a metallic material.

7. The locking system of claim 1, wherein the flexible member disposed on the guide wire provides shock absorbing capabilities to at least partially absorb unwanted shock that may be transmitted along the guide wire to the locking component.

8. The locking system of claim 1, wherein the flexible member disposed on the guide wire provides shock absorbing capabilities to at least partially absorb unwanted shock that may be transmitted along the guide wire to the medical device.

9. The locking system of claim 1, wherein the means for temporarily compressing the flexible body member of the guide wire is a tubular member having a longitudinal opening adapted to receive and temporarily compress at least a portion of the flexible body member.

10. The locking system of claim 9, wherein the longitudinal opening of the tubular member is proximally tapered from one diameter to a smaller diameter.

11. The locking system of claim 10, wherein the recess formed in the locking device is adjacent to the smaller diameter of the longitudinal opening and in communication with the longitudinal opening.

12. The locking system of claim 9, wherein the tubular member includes a flange at on end which is disposed in the recess formed in the body member.

13. The locking system of claim 9, wherein the body member of the locking component includes a guide wire lumen which slidably receives the guide wire.

14. A system for locking a component along a guide wire, comprising:
   a guide wire having a flexible body member disposed thereon;
   a locking component having a body member including means for temporarily compressing at least a portion of the flexible body member of the guide wire to allow the compressed portion of the flexible body member to be placed in a recess formed in the body member, the compressed portion of the flexible body member being adapted to decompress within the recess to lock the formerly compressed portion of the flexible body member within the recess, the means for temporarily compressing the flexible body member of the guide wire being a longitudinal opening extending into the body member which is adapted to receive and temporarily compress at least a portion of the flexible body member, the recess formed in the locking device being adjacent to the smaller diameter of the longitudinal opening and in communication with the longitudinal opening, the longitudinal opening extending into the body member being proximally tapered from one diameter to a smaller diameter; and
   a medical device which is deliverable over the guide wire and coupled to the locking component, wherein the flexible body member of the guide wire is a helical coil disposed on the guide wire and the smallest diameter of the tapered, longitudinal opening is smaller than the diameter of the helical coil.

15. The locking system of claim 14, wherein the helical coil disposed on the guide wire is at the distal end of the guide wire.

16. An embolic protection device, comprising:
   a guide wire including a flexible body member fixedly attached thereon;
   a filter assembly having a proximal end and a distal end; and
   a guide wire locking component attached to one of the ends of the filter assembly, the guide wire locking component being movable along the guide wire and including means for temporarily compressing at least a portion of the flexible body member of the guide wire to allow the compressed portion of the flexible body member to be placed in a recess formed in the guide wire locking component, the compressed portion of the flexible body member being adapted to decompress within the recess to lock the formerly compressed portion of the flexible body member within the recess.

17. The embolic protection device of claim 16, wherein the guide wire locking component defines a body member and the means for temporarily compressing the flexible body member of the guide wire is a longitudinal opening extending into the body member which is adapted to receive and temporarily compress at least a portion of the flexible body member.

18. The embolic protection device of claim 17, wherein the longitudinal opening extending into the body member is proximally tapered from one diameter to a smaller diameter.

19. The embolic protection device of claim 18, wherein the recess formed in the locking device is adjacent to the smaller diameter of the longitudinal opening and the recess is in communication with the longitudinal opening.

20. The embolic protection device of claim 19, wherein the flexible body member of the guide wire is a helical coil disposed on the guide wire and the smallest diameter of the tapered, longitudinal opening is smaller than the diameter of the helical coil.

21. The embolic protection device of claim 20, wherein the helical coil disposed on the guide wire is at the distal end of the guide wire.

22. The embolic protection device of claim 16, wherein the flexible member disposed on the guide wire provides shock absorbing capabilities to at least partially absorb unwanted shock that may be transmitted along the guide wire to the filter assembly.

23. The embolic protection device of claim 16, wherein the flexible member disposed on the guide wire is a coil spring.

24. An apparatus for embolic protection, comprising:
a guide wire having a flexible body member attached thereto;
a filter assembly disposed for traveling along the guide wire, the filter assembly including a first end and a second end; and
a guide wire locking component disposed on one of the ends of the filter assembly, the guide wire locking component including a longitudinal opening extending into the body member which is adapted to receive and temporarily compress at least a portion of the flexible body member to allow the compressed portion of the flexible body member to placed in a recess formed in the guide wire locking component, the compressed portion of the flexible body member being adapted to decompress within the recess to lock the formerly compressed portion of the flexible body member within the recess.

25. The apparatus of claim 24, wherein the longitudinal opening extending into the locking component is tapered from one diameter to a smaller diameter.

26. The apparatus of claim 25, wherein the recess formed in the locking device is adjacent to the smaller diameter of the longitudinal opening and the recess is in communication with the longitudinal opening.

27. The apparatus of claim 24, wherein the flexible body member is rotatable attached to the guide wire.

28. The apparatus of claim 24, wherein the flexible body member is a helical coil disposed at the distal end of the guide wire.

29. The apparatus of claim 24, wherein the flexible body member is a helical coil.

30. The apparatus of claim 29, wherein the helical coil include a tapered proximal end.

31. The apparatus of claim 30, wherein the tapered proximal end of the helical coil is stretched to form gaps between adjacent coils.

32. The apparatus of claim 24, further including a delivery sheath enclosing the filter assembly and used to advance the filter assembly along the guide wire.

33. An apparatus for embolic protection, comprising:
a guide wire having a flexible body member rotatably mounted on the guide wire;
a filter assembly including a proximal end and a distal end; and
a guide wire locking component attached to one of the ends of the filter assembly, the guide wire locking component including means for temporarily compressing at least a portion of the flexible body member of the guide wire to allow the compressed portion of the flexible body member to placed in a recess formed in the guide wire locking component, the compressed portion of the flexible body member being adapted to decompress within the recess to lock the formerly compressed portion of the flexible body member within the recess while allowing the filter assembly to be rotatable relative to the guide wire.

34. The apparatus of claim 33, wherein the rotating flexible body member is disposed between a pair of stop fittings.

35. The apparatus of claim 34, wherein the guide wire includes a proximal coil section and a distal coil section and the rotating flexible body member is disposed between the proximal coil section and the distal coil section.

* * * * *